(12) United States Patent
Byrum et al.

(10) Patent No.: US 7,351,198 B2
(45) Date of Patent: Apr. 1, 2008

(54) IMPLANTABLE ADJUSTABLE SPHINCTER SYSTEM

(75) Inventors: Randal T. Byrum, Loveland, OH (US); Thomas W. Huitema, Cincinnati, OH (US); William L. Hassler, Jr., Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 312 days.

(21) Appl. No.: 10/858,696

(22) Filed: Jun. 2, 2004

(65) Prior Publication Data

US 2005/0272968 A1 Dec. 8, 2005

(51) Int. Cl.
*A61F 2/02* (2006.01)

(52) U.S. Cl. ..................................... 600/31

(58) Field of Classification Search ............ 600/9–15, 600/29–32, 38–41; 623/14.13; 604/96.01; 128/897–899
See application file for complete search history.

(56) References Cited

U.S. PATENT DOCUMENTS

| | | |
|---|---|---|
| 4,342,308 A | 8/1982 | Trick |
| 4,360,010 A | 11/1982 | Finney |
| 4,404,968 A | 9/1983 | Evans, Sr. |
| 4,428,365 A | 1/1984 | Hakky et al. |
| 4,441,491 A | 4/1984 | Evans, Sr. |
| 4,574,792 A | 3/1986 | Trick |
| 4,581,018 A | 4/1986 | Jassawalla et al. |
| 4,592,339 A | 6/1986 | Kuzmak et al. |
| 4,782,826 A | 11/1988 | Fogarty |
| 4,823,779 A | 4/1989 | Daly et al. |
| 4,898,158 A | 2/1990 | Daly et al. |
| 4,958,630 A * | 9/1990 | Rosenbluth et al. .......... 600/40 |
| 5,152,770 A | 10/1992 | Bengmark et al. |
| 5,154,693 A | 10/1992 | East et al. |
| 5,167,615 A | 12/1992 | East et al. |
| 5,226,429 A | 7/1993 | Kuzmak |
| 5,230,694 A | 7/1993 | Rosenblum |
| 5,449,368 A | 9/1995 | Kuzmak |
| 5,507,737 A | 4/1996 | Palmskog |
| 5,509,888 A * | 4/1996 | Miller ......................... 600/29 |
| 5,637,083 A | 6/1997 | Bertrand et al. |
| 5,715,837 A | 2/1998 | Chen |
| 5,733,313 A | 3/1998 | Barreras, Sr. et al. |

(Continued)

FOREIGN PATENT DOCUMENTS

GB 2 355 937 5/2001

(Continued)

*Primary Examiner*—Charles A Marmor, II
*Assistant Examiner*—Christine D Hopkins
(74) *Attorney, Agent, or Firm*—Frost Brown Todd, LLC

(57) ABSTRACT

An implantable adjustable sphincter system is comprised of a band configured to encircle a portion of an anatomical passageway, a manual pump, a reservoir in fluid communication with the pump, and a valve assembly in fluid communication with the band and the manual pump. The valve assembly is comprised of a first configuration and a second configuration, and is operable to be manually switched between configurations. The first configuration only permits fluid to flow from the band toward the reservoir. The second configuration only permits fluid to flow from the reservoir toward the band. The manual pump is in fluid communication with the valve assembly and the reservoir, and is manually operable to transfer fluid between the reservoir and the band when the valve assembly is in the second configuration.

20 Claims, 2 Drawing Sheets

U.S. PATENT DOCUMENTS

| | | | |
|---|---|---|---|
| 5,749,909 A | 5/1998 | Schroeppel et al. | |
| 5,938,669 A | 8/1999 | Klaiber et al. | |
| 5,974,873 A | 11/1999 | Nelson | |
| 6,058,330 A | 5/2000 | Borza | |
| 6,067,991 A * | 5/2000 | Forsell | 128/899 |
| 6,102,678 A | 8/2000 | Peclat | |
| 6,102,922 A | 8/2000 | Jakobsson et al. | |
| 6,315,769 B1 | 11/2001 | Peer et al. | |
| 6,366,817 B1 | 4/2002 | Kung | |
| 6,430,444 B1 | 8/2002 | Borza | |
| 6,432,040 B1 * | 8/2002 | Meah | 600/37 |
| 6,443,887 B1 | 9/2002 | Derus et al. | |
| 6,461,292 B1 | 10/2002 | Forsell | |
| 6,463,329 B1 | 10/2002 | Goedeke | |
| 6,470,892 B1 * | 10/2002 | Forsell | 128/899 |
| 6,475,136 B1 * | 11/2002 | Forsell | 600/37 |
| 6,482,145 B1 * | 11/2002 | Forsell | 600/30 |
| 6,482,177 B1 | 11/2002 | Leinders | |
| 6,533,719 B2 | 3/2003 | Kuyava et al. | |
| 6,542,350 B1 | 4/2003 | Rogers | |
| 7,060,080 B2 * | 6/2006 | Bachmann | 606/151 |
| 2001/0041823 A1 * | 11/2001 | Snyder et al. | 600/31 |
| 2003/0100929 A1 * | 5/2003 | Forsell | 607/39 |
| 2003/0105385 A1 | 6/2003 | Forsell | |
| 2003/0114729 A1 | 6/2003 | Forsell | |
| 2003/0163079 A1 | 8/2003 | Burnett | |

FOREIGN PATENT DOCUMENTS

| | | |
|---|---|---|
| WO | WO 90/04368 | 5/1990 |
| WO | WO 00 72899 | 12/2000 |

* cited by examiner

IMPLANTABLE ADJUSTABLE SPHINCTER SYSTEM

TECHNICAL FIELD

The present invention relates in general to surgically implantable device systems, and more particularly, to an implantable adjustable band system.

BACKGROUND OF THE INVENTION

Since the early 1980s, adjustable gastric bands have provided an effective alternative to gastric bypass and other irreversible surgical weight loss treatments for the morbidly obese. The gastric band is typically wrapped around an upper portion of the patient's stomach, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band.

In addition to a latched position to set the outer diameter of the gastric band, adjustability of gastric bands is generally achieved with an inwardly directed inflatable balloon, similar to a blood pressure cuff. The inner diameter of the gastric band may thereby be adjusted by adjusting the pressure in the balloon. Typically, a fluid such as saline is injected into the balloon through a fluid injection port to achieve a desired diameter. Since adjustable gastric bands may remain in the patient for long periods of time, the fluid injection port is typically installed subcutaneously to avoid infection, for instance in front of the sternum. Adjusting the amount of fluid in the adjustable gastric band is typically achieved by inserting a Huber tip needle through the skin into a silicon septum of the injection port. Once the needle is removed, the septum seals against the hole by virtue of compressive load generated by the septum. A flexible conduit communicates between the injection port and the adjustable gastric band.

The traditional surgical technique for securing a fluid injection port developed for vascular uses has been applying sutures through a series of holes spaced about a peripheral base flange. While generally effective, suturing often proves to be difficult since adjustable gastric bands are intended for the morbidly obese. A significant thickness of fat tissue may underlie the skin, causing difficulties as the surgeon attempts to apply sutures to deeply recessed tissues (e.g., 10-12 cm) to secure the port, often requiring 10-15 minutes to complete.

In addition to the difficulty of installing an injection port, the use of injections and injection ports for adjusting gastric bands has other disadvantages apparent to those of ordinary skill in the art. For example, port-site infections are a common complication arising from the use of injection ports. In addition, the use of needles or other invasive techniques to adjust a gastric band may subject a patient to unnecessary discomfort.

The art includes some gastric band adjustment systems that do not require the use of injections or injection ports, such as employing an electrical motor that adjusts the volume of a bellows accumulator. Power to such an implant is generally provided by transcutaneous energy transfer (TET), with control and/or feedback provided by telemetry. Such TET systems have to overcome design challenges associated with electromagnetic interference and compatibility (EMIC). In addition, a clinician who adjusts the adjustable gastric band has to invest in the external equipment necessary for TET.

Implant systems exist that employ the use of manually palpable pumps and valve assemblies in the context of penile implant systems. An example of such a system is disclosed in U.S. Pat. No. 4,404,968, issued to Evans. However, in contrast to the present invention, such penile implant systems employ the use of generally linear bladders as opposed to adjustable sphincters. In addition, such penile implants provide obvious visual feedback as to which direction the fluid in the implant system is flowing. The pumps in many conventional penile implant systems are bulbs located in the scrotum, such that the pump may be easily palpated by hand through relatively thin skin by squeezing both sides of the bulb.

Accordingly, it would be advantageous to have an implantable system whereby an adjustable sphincter, such as a gastric band, may be adjusted without the use of an injection or injection port. It would be further advantageous to have such a system that avoids the inconveniences of conventional TET implant systems. Consequently, a significant need exists for an implantable adjustable sphincter system that is percutaneously adjustable without the use of injections, an injection port, or TET.

BRIEF SUMMARY OF THE INVENTION

The present invention addresses these and other problems in the prior art by providing an implantable adjustable sphincter system comprising a band, a reservoir, a valve assembly, and a manual pump that may be simply palpated to increase and/or decrease the size of a stoma formed by the band acting as a sphincter.

In one aspect of the invention, there is an implantable adjustable sphincter system for treatment of a medical condition. The system is comprised of a band configured to encircle a portion of an anatomical passageway and to resiliently receive and hold fluid. The system is further comprised of a manual pump responsive to manual palpation and a reservoir in fluid communication with the manual pump. The system is further comprised of a valve assembly in fluid communication with the band and the manual pump. The valve assembly is comprised of a first configuration and a second configuration. The first configuration permits fluid from the band to flow toward the reservoir. The first configuration also prevents fluid from flowing from the reservoir toward the band. The second configuration permits fluid from the reservoir to flow toward the band. The second configuration also prevents fluid from flowing from the band toward the reservoir. The valve assembly is operable to be manually switched between the first configuration and second configuration. The manual pump is in fluid communication with the valve assembly and the reservoir. The manual pump is manually operable to transfer fluid between the reservoir and the band in response to manual palpation when the valve assembly is in the second configuration. Thus, neither an injection port nor the use of injections or TET is required to adjust the size of the stoma created by the band.

These and other objectives and advantages of the present invention shall be made apparent from the accompanying drawings and the description thereof.

BRIEF DESCRIPTION OF THE DRAWINGS

The accompanying drawings incorporated in and forming a part of the specification illustrate several aspects of the present invention, and, together with the description, serve to explain the principles of the invention. In the drawings.

Reference will now be made in detail to the present preferred embodiment of the invention, an example of which is illustrated in the accompanying drawings.

DETAILED DESCRIPTION

Figure 1:
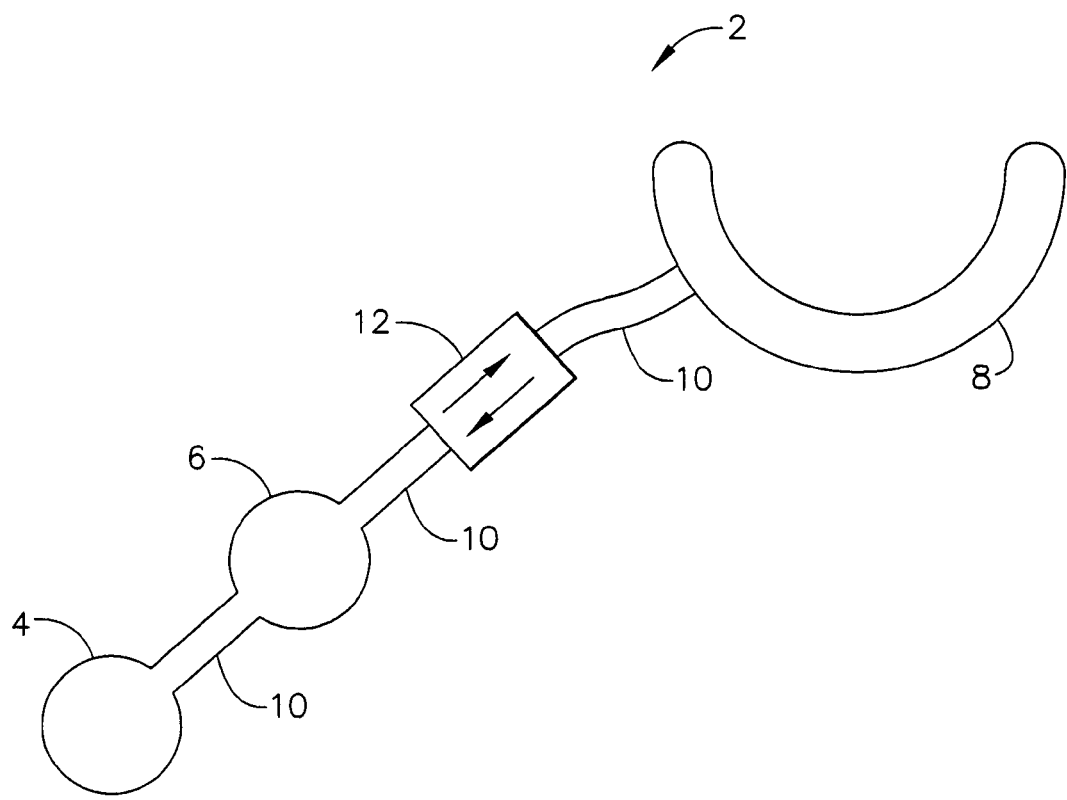
FIG. 1 is a diagrammatic view of an implantable adjustable sphincter system.

Referring now to the drawings in detail, wherein like numerals indicate the same elements throughout the views, FIG. 1 shows an adjustable gastric band system 2. The system 2 is comprised of a reservoir 4, a pump 6, a valve assembly 12, and an adjustable gastric band 8. In the present example, a flexible conduit 10 connects the reservoir 4 to the pump 6, the pump 6 to the valve assembly 12, and the valve assembly 12 to the band 8. Each portion of the conduit 10 thus serves as a means of fluid communication between each component that the conduit 10 connects. It will be appreciated, however, that two or more components may be situated and/or constructed such that the components may fluidly communicate without the need for a conduit 10. By way of example only, the pump 6 may be integrally connected to the reservoir 4. In addition, or alternatively, the pump 6 may be integrally connected to the valve assembly 12. Such types of alternate configurations of the system 2 will not result in departure from the scope of the present invention.

In the present example, the reservoir 4 is configured to hold fluid, such as saline for example. The reservoir 4 may be made of silicone, for example, or any other suitable biocompatible material. Preferably, the reservoir 4 will be generally deformable or resilient. The function of the reservoir 4 relative to the system 2 as a whole will be apparent to those of ordinary skill in the art.

As is known in the art, the adjustability of a gastric band 8 may be a function of band 8 fluid pressure or volume. In the present example, the pump 6 may be used to increase band 8 pressure or volume when the valve assembly 12 is configured to allow fluid to be pumped into the band 8 without allowing fluid to escape from the band 8. The pump 6 in the present example is a silicone bulb, however any suitable biocompatible alternative may be used. With the valve assembly 12 properly configured, the pump 6 in the present example may be manually palpated to draw fluid from the reservoir 4 toward the band 8, thereby increasing the band 8 pressure or volume. As will be apparent to those of ordinary skill in the art, this increase in band 8 pressure or volume will result in a reduction in the size of the stoma in the stomach in the present example.

As the pump 6 may be located subcutaneously, the pump 6 may be palpated by manually applying pressure on the skin above the site where the pump 6 is located. Alternatively, the pump 6 may be palpated by the flexing of the abdominal muscles or other bodily function. Preferably, the pump 6 should be sized to pump an appropriate amount of fluid while not being too obtrusive to the patient.

The valve assembly 12 may be comprised of two one-way valves. Alternatively, the valve assembly 12 may be comprised of a single one-way valve configured such that its direction may be switched. Still other possible ways of making the valve assembly 12 will be apparent to those of ordinary skill in the art.

The valve assembly 12 is comprised of one or more configurations, such that each configuration may dictate whether and in which direction fluid may flow through the system 2. A first configuration may permit fluid from the band 8 to flow toward the reservoir 4, while preventing fluid from flowing from the reservoir 4 toward the band 8. This first configuration would thus be used when the band 8 pressure or volume is to be decreased, thereby allowing the size of the stoma in the stomach to increase. This flow of fluid may occur as a result of a pressure differential across the valve assembly 12. This flow of fluid may also be made to occur by pumping. As will be apparent to those of ordinary skill in the art, the pump 2 may be constructed such that it is operable to pump fluid from the band 8 toward the reservoir 4 when the valve assembly 12 is in this first configuration.

Alternatively, there could be a plurality of pump-valve systems such as, by way of example only, two pumps and two valves, each being operable to draw fluid from or toward the band 8, respectively.

Following the present example having one valve assembly 12, a second configuration of the valve assembly 12 may permit fluid from the reservoir 4 to flow toward the band 8, while preventing fluid from flowing from the band 8 toward the reservoir 4. This second configuration would be used when the band 8 pressure or volume is to be increased, thereby causing the size of the stoma in the stomach to decrease. In the present example, this flow of fluid would be made to occur as a result of manual palpation of the pump 6.

It is understood that, in the present example, manual palpation of the pump 6, while the valve assembly 12 is in the first configuration, may result in fluid circulating within the reservoir 4 and/or fluid flowing from the reservoir 4 toward the pump 6 and/or toward the valve assembly 12. Incidentally, this flow may be in the general direction of the band 8. Nevertheless, such flow will not result in departure from the scope of the language defining the first configuration in part as preventing fluid from flowing from the reservoir toward the band. Ultimately, the first configuration would prevent fluid from flowing through the entire valve assembly 12 into the band 8.

In addition, while the manual pump 6 may be described as being manually operable to transfer fluid between the reservoir 4 and the band 8, it will be apparent to those of ordinary skill in the art that such language should not be read as limiting the invention to require the pump 6 to actually transfer fluid from the reservoir 4 into the band 8. In other words, pressure in the band 8 may be increased by the mere shifting of fluid in the reservoir 4 toward the band 8, as such shifting will cause similar shifting of fluid "upstream" of the reservoir 4 when the valve assembly 12 is in the second configuration. It is not necessary for fluid being introduced into the band 8 by palpation of the pump 6 to have actually come from the reservoir 4. Consistent with the present invention, this additional fluid may originate from any part of the system 2 between the band 8 and the reservoir 4.

A third configuration of the valve assembly 12 may prevent fluid from flowing through the valve assembly 12 at all. This third configuration may thereby prohibit fluid from flowing into or out of the band 8. In other words, the third configuration may be considered as the valve assembly 12 being bi-directionally "closed." Thus, this third configuration may be used when the band 8 pressure or volume is sought to be maintained. Preferably, the valve assembly 12 will be in this third configuration by default. In other words, it may be desirable to keep the valve assembly 12 in the third configuration most of the time, only switching it to the first or second configuration when it is desired that the band 8 pressure or volume be decreased or increased, respectively.

It will be appreciated that, without actual palpation of the pump 6, the second configuration of the valve assembly 12 may be all that is necessary to maintain band 8 pressure or volume. In other words, a valve assembly 12 may be constructed within the present invention without having a third configuration. However, having a third configuration of the valve assembly 12 may be preferable to the extent that it may prevent inadvertent increase in band 8 pressure or volume. That is, to the extent that the pump 6 may be unintentionally palpated by incidental pressure on the pump 6, such as pressure caused by leaning against a table for example, the third configuration of the valve assembly 12 would prevent such unintentional palpation from causing the pressure or volume of the band 8 to increase. Nevertheless, where a valve assembly 12 is constructed having only a first and second configuration, the valve assembly 12 may be considered "closed" in the second configuration to the extent that palpation of the pump 6 is required to create sufficient pressure to overcome and open a valve.

The valve assembly 12 may be constructed such that the valve assembly 12 may be switched between the various configurations by way of a mechanism responsive to manual palpation. By way of example only, the valve assembly 12 may be constructed such that the configuration of the valve assembly 12 may be switched by percutaneous manipulation of a switch, lever, dial, button, or any other suitable switching alternative or combination thereof. Where the valve assembly 12 configuration is manually switchable by such a mechanism or mechanisms, the valve assembly 12 may give tactile feedback indicating the configuration of the valve assembly 12 based on the position of the switching mechanism or mechanisms.

Alternatively, the valve assembly 12 may be constructed such that the valve assembly 12 may be switched between configurations by the transcutaneous transmission of other non-electromagnetic energy to the valve assembly 12. By way of example only, a valve assembly 12 may be constructed such that the valve assembly 12 may be switched between configurations by way of ultrasound. In other words, a valve assembly 12 may be made responsive to ultrasound such that valves are actuated or the valve assembly 12 is otherwise placed in various configurations by mechanical resonance and/or other effects created by ultrasound.

The valve assembly 12 may be made to respond differently to different frequencies of ultrasound. For example, a first frequency may actuate a first valve or otherwise place the valve assembly 12 in a first configuration, such that fluid is permitted to flow from the band 8 toward the reservoir 4, while fluid is prevented from flowing from the reservoir 4 toward the band 8. A second frequency may actuate a second valve or otherwise place the valve assembly 12 in a second configuration, such that fluid is permitted to flow from the reservoir 4 toward the band 8, while fluid is prevented from flowing from the band 8 toward the reservoir 4. A third frequency may place the valve assembly 12 in a third configuration, such that fluid would be prevented from flowing through the valve assembly 12 at all. Alternatively, the valve assembly 12 may be constructed such that the valve assembly 12 is in such a third configuration by default (i.e. when it is not being exposed to a first or second frequency of ultrasound). In such an embodiment, the response of the valve assembly 12 to the first and/or second frequency may be substantially temporally limited to the duration of the exposure of the valve assembly 12 to the first and/or second frequency, respectively. In other words, the valve assembly 12 may be constructed such that the valve assembly 12 would be placed in the first or second configuration only for the approximate time of its exposure to the first or second frequency, respectively.

Alternatively, the adjustment may be enabled by a wide range of ultrasonic frequencies, relying upon sufficient strength of ultrasonic energy to avoid inadvertent enablement. Even given brief exposure to ultrasonic energy, such as for a medical diagnostic procedure wherein adjustment is not intended, integrating primary value control with pumping may ensure maintenance of fluid pressure. The ultrasonic energy may assist in overcoming static friction, for instance, within dynamic seals of the pump that enable pumping to occur, which would otherwise resist movement.

In such an ultrasonically enabled valve assembly 12, direction of adjustment may be controlled by having the pump 6 comprised of two parallel pumps, each check valve controlled to allow fluid in opposite directions with each opposing all flow when in an unactuated state. Thus, the ultrasonic enablement avoids inadvertent actuation of the pumps, yet specifically tailored ultrasonic sources need not be used.

Figure 2:
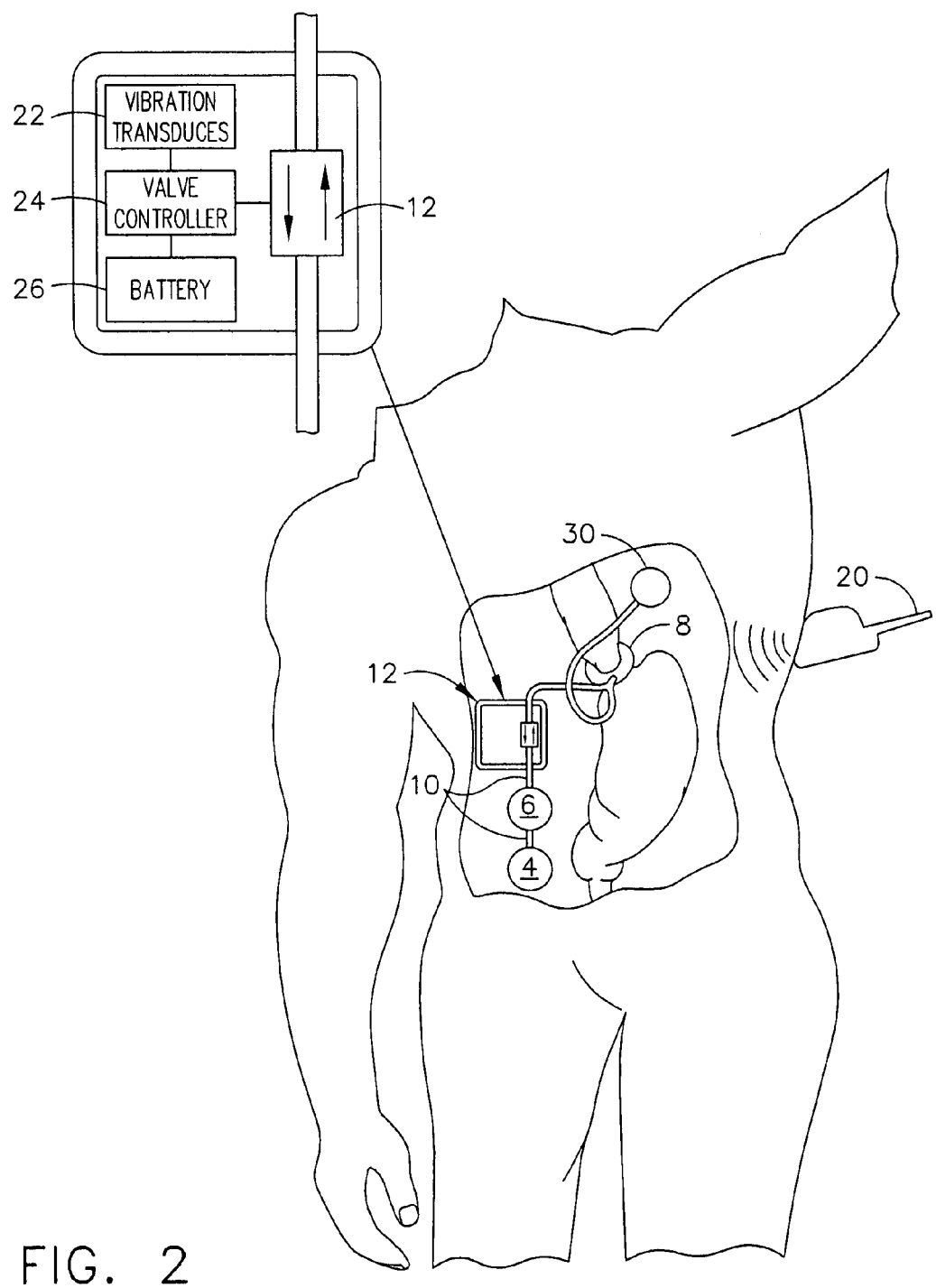
FIG. 2 is a view of an implanted adjustable gastric band system having an ultrasonically activated valve assembly.

As another example in FIG. 2, an electrically-powered valve controller 24 may be energized or activated by an ultrasonic frequency coming from an ultrasound emitter 20, such as with a vibration transducer 22, and electromechanically actuate a valve or valves in response thereto, or otherwise change configurations of the valve assembly 12 in response to an ultrasonic frequency. In this embodiment, the valve assembly 12 may be coupled with or include such a transducer 22 and controller 24, along with a battery 26 as a source of power to the valve or valves. As merely providing power to a valve or valves, such a battery 26 may have a longer life than a battery that supplies power to a pump, such as those found in conventional TET-operated implant systems. Additionally, the valve assembly 12, including the transducer 22, controller 24, and battery 26, may all be electrically shielded to avoid EMIC considerations that are typically appurtenant to conventional TET systems.

As to any embodiment where the valve assembly 12 is responsive to ultrasound, it may be desirable to limit the responsiveness of the valve assembly 12 to certain patterns of ultrasound. That is, rather than being immediately responsive to a certain frequency or frequencies of ultrasound, the valve assembly 12 could be made such that the valve assembly 12 will only respond to a frequency or frequencies of ultrasound being emitted in a certain pattern or patterns. By way of example only, such pattern-based requirements may alleviate concerns that the valve assembly may respond to ultrasound being emitted by unforeseen sources of ultrasound.

The process of implanting conventional gastric band systems is known in the art and therefore needs not be reiterated in detail herein. By way of example, the implantation of gastric band systems using injection ports is described in one or more of the following U.S. patents: U.S. Pat. No. 4,592,339 issued on Jun. 3, 1986 to Kuzmak et al.; U.S. Pat. No. 5,226,429 issued on Jul. 13, 1993 to Kuzmak; U.S. Pat. No. 6,102,922 issued on Aug. 15, 2000 to Jakobsson et al.; and U.S. Pat. No. 5,449,368 issued on Sep. 12, 1995 to Kuzmak. Each of the above-listed patents is assigned to the assignee of the present invention and is incorporated herein by reference. While the gastric bands in the above-cited patents employ the use of injection ports as the sole means to adjust the gastric band, as opposed to a pump 6 and valve assembly 12, the implantation and function of the bands themselves are similar to the band 8 in the present example.

As to the band 8 in the present example, the method of securing the band 8 around the stomach may be accomplished using conventional methods. The rest of the components of the system may also be implanted subcutaneously. By way of example only, the valve assembly 12, pump 6, and reservoir 4 may all be implanted anywhere convenient in the abdominal cavity. Alternatively, any or all of the components may be implanted in any other suitable location. Any or all of the components may be attached to a suitable surface within the body. Alternatively, any or all of the components may be attached to no surface within the body.

Preferably, the pump 6 will be implanted in the abdominal cavity. In this way, the pump 6 may be percutaneously palpated through relatively thick abdominal skin from one side only. The pump 6 may be placed against fascia that resists inward pressure to allow pumping by applying pressure on the side of the pump 6 opposite to the fascia.

Once the band 8 and the components are in place, the pressure or volume of the band 8 may be brought to an initial desired level, in accordance with the initial desired size of the stoma created in the stomach by the band 8. For example, the system 2 may be implanted with all of the fluid already inside the system 2, such that palpation of the pump 6 is all that is necessary to bring the pressure or volume of the band 8 to an initial desired level, such as through an injection port 30. Alternatively, the system 2 may be implanted with less than all desired fluid inside the system 2, such that additional fluid is added to the system 2 shortly following implantation. By way of example only, where additional fluid is to be added to the system 2 shortly following implantation, such additional fluid may be added by injecting the fluid into a port on a component of the system 2. Still other ways of achieving an initial desired band 8 pressure or volume will be apparent to those of ordinary skill in the art.

In use, a time may come where it is desired to have the band 8 pressure or volume decreased or increased. Where a decrease in band 8 pressure or volume is desired, the valve assembly 12 will be manually switched to the first configuration. Then, due to the fluid pressure being higher on the band 8 side of the valve assembly 12 than the fluid pressure on the other side of the valve assembly 12, fluid will tend to drain toward the reservoir 4 end of the system 2 until the pressure throughout the system 2 is generally uniform. Alternatively or additionally, fluid may be drawn from the band 8 toward the reservoir 4 by manual palpation of the pump 6. When the desired amount of pressure or volume has been relieved from the band 8, the valve assembly 12 may then be switched to the second or third configuration to prevent additional fluid from escaping the band 8.

Where an increase in band 8 pressure or volume is desired, and the valve assembly 12 is not already in the second configuration, the valve assembly 12 will be manually switched to the second configuration. Then, the pump 6 will be palpated to draw fluid from the reservoir 4 and force it toward the band 8, thereby increasing the band 8 pressure or volume. When the desired amount of pressure or volume has been added to the band 8, the person palpating the pump 6 should cease palpating the pump 6. The valve assembly 12 may then be left in the second configuration, or alternatively, switched to the third configuration.

It will become readily apparent to those skilled in the art that the above invention has equal applicability to other types of implantable bands or adjustable sphincters. For example, bands may be used for the treatment of fecal incontinence. One such band is described in U.S. Pat. No. 6,461,292, which is incorporated herein by reference. Bands may also be used to treat urinary incontinence. One such band is described in U.S. Patent Application 2003/0105385, which is incorporated herein by reference. Bands may also be used to treat heartburn and/or acid reflux. One such band is described in U.S. Pat. No. 6,470,892, which is incorporated herein by reference. Bands may also be used to treat impotence. One such band is described in U.S. Patent Application 2003/0114729, which is incorporated herein by reference.

In summary, numerous benefits have been described which result from employing the concepts of the invention. While preferred embodiments of the present invention have been shown and described herein, it will be obvious to those skilled in the art that such embodiments are provided by way of example only. The foregoing description of one or more embodiments of the invention has been presented for purposes of illustration and description. It is not intended to be exhaustive or to limit the invention to the precise form disclosed. Obvious modifications or variations are possible in light of the above teachings without departing from the invention. For example, a reservoir may include a pressure differential to the band such that one of the valve positions is sufficient to create a change in fluid volume with the band without manual pumping. A bellows accumulator within a sealed case containing a propellant that asserts a differential pressure is one such reservoir.

It should be understood that every structure described above has a function and such structure can be referred to as a means for performing that function. The one or more embodiments were chosen and described in order to best illustrate the principles of the invention and its practical application to thereby enable one of ordinary skill in the art to best utilize the invention in various embodiments and with various modifications as are suited to the particular use contemplated. Accordingly, it is intended that the invention be limited only by the spirit and scope of the appended claims.

What is claimed is:

1. An implantable adjustable sphincter system for treatment of a medical condition of a patient comprising:
   (a) a band configured to encircle a portion of an anatomical passageway and to resiliently receive and hold fluid;
   (b) a manual pump responsive to manual palpation;
   (c) a reservoir in fluid communication with said manual pump; and
   (d) a valve assembly in fluid communication with said band and said manual pump, said valve assembly comprising:
      (i) a first configuration, wherein said first configuration permits fluid from the band to flow toward the reservoir, wherein said first configuration prevents fluid from flowing from the reservoir toward the band; and
      (ii) a second configuration, wherein said second configuration permits fluid from the reservoir to flow toward the band, wherein said second configuration prevents fluid from flowing from the band toward the reservoir;
   wherein said valve assembly is operable to be switched between said first configuration and said second configuration; wherein said manual pump is in fluid communication with said valve assembly and said reservoir, wherein said manual pump is manually operable to transfer fluid between said reservoir and said band in response to manual palpation when said valve assembly is in said second configuration;

wherein said manual pump is adapted to be implanted within a patient's body against fascia that resists inward pressure; and wherein said valve assembly provides percutaneous tactile feedback indicating whether said valve assembly is in said first configuration or said second configuration;

wherein said valve assembly further comprises a mechanism responsive to ultrasound, wherein said valve assembly is operable to be placed in the first configuration in response to a first ultrasound emission, and wherein said valve assembly is operable to be placed in the second configuration in response to a second ultrasound emission.

2. The implantable adjustable sphincter system of claim 1, wherein said valve assembly is operable to be switched between said first configuration and said second configuration percutaneously.

3. The implantable adjustable sphincter system of claim 1, wherein said manual pump further comprises a silicone bulb.

4. The implantable adjustable sphincter system of claim 1, said valve assembly further comprising a third configuration, wherein said third configuration prohibits fluid from flowing into or out of the band, wherein said valve assembly is operable to be switched between said first configuration, said second configuration, and said third configuration.

5. The implantable adjustable sphincter system of claim 1, wherein said valve assembly further comprises a mechanism responsive to manual palpation, wherein said mechanism is operable to switch said valve assembly between the first configuration, the second configuration, and the third configuration in response to manual palpation.

6. The implantable adjustable sphincter system of claim 1, wherein said first ultrasound emission is at a first ultrasound frequency, wherein said second ultrasound emission is at a second ultrasound frequency.

7. The implantable adjustable sphincter system of claim 1, wherein said first ultrasound emission is in a first pattern, wherein said second ultrasound emission is in a second pattern.

8. An implantable adjustable sphincter system for treatment of obesity, comprising:
  a band configured to encircle a portion of the patient's stomach and to resiliently receive and hold fluid;
  a manual pump responsive to manual palpation; and
  a valve assembly in fluid communication with said band and said manual pump, said valve assembly comprising:
    a first configuration, wherein said first configuration permits fluid to flow away from the band and prevents fluid from flowing toward the band, and
    a second configuration, wherein said second configuration permits fluid to flow toward the band and prevents fluid from flowing away from the band and
    a third configuration, wherein said third configuration prohibits fluid from flowing into or out of the band;
  wherein said valve assembly further comprises a mechanism responsive to ultrasound, wherein said valve assembly is operable to be placed in the first configuration in response to a first ultrasound emission, wherein said valve assembly is operable to be placed in the second configuration in response to a second ultrasound emission, and wherein said valve assembly is operable to be placed in the third configuration in response to a third ultrasound emission;
  wherein said manual pump is in fluid communication with said valve assembly and said band; and
  wherein said manual pump is manually operable to transfer fluid to said band in response to manual palpation when said valve assembly is in said second configuration.

9. A method of using an implantable adjustable sphincter system for treatment of obesity, the method comprising:
  (a) providing a gastric band system, wherein the gastric band system comprises:
    (i) a gastric band, wherein the gastric band is sized and configured to encircle a portion of the patient's stomach and to resiliently receive and hold fluid,
    (ii) a manual pump responsive to manual palpation,
    (iii) a reservoir in fluid communication with said manual pump, and
    (iv) a valve assembly in fluid communication with said band and said manual pump, said valve assembly comprising:
      a first configuration, wherein said first configuration permits fluid from the band to flow toward the reservoir, wherein said first configuration prevents fluid from flowing from the reservoir toward the band,
      a second configuration, wherein said second configuration permits fluid from the reservoir to flow toward the band, wherein said second configuration prevents fluid from flowing from the band toward the reservoir, and
      a third configuration, wherein said third configuration prohibits fluid from flowing into or out of the band;
    wherein said valve assembly is operable to be switched between said first configuration, said second configuration, and said third configuration;
    wherein said manual pump is in fluid communication with said valve assembly and said reservoir, wherein said manual pump is manually operable to transfer fluid between said reservoir and said band in response to manual palpation when said valve assembly is in said second configuration;
  (b) securing the gastric band about an upper portion of a patient's stomach, thereby forming a stoma;
  (c) increasing pressure in the band to reduce the size of the stoma, thereby restricting passage of food from the upper portion of the patient's stomach to a lower portion of the patient's stomach, without completely preventing passage of food through the stoma into the lower portion of the patient's stomach; and
  (d) maintaining the pressure in the band obtained as a result of the act of increasing pressure.

10. The method of claim 9, wherein the act of increasing pressure in the band comprises manually palpating the manual pump.

11. The method of claim 9, further comprising reducing pressure in the band to increase the size of the stoma.

12. The method of claim 11, wherein the act of reducing pressure comprises manually palpating the manual pump.

13. The method of claim 9, wherein the valve assembly comprises at least two one-way valves.

14. The method of claim 9, wherein said valve assembly is operable to be switched between said first configuration and said second configuration percutaneously.

15. The method of claim 9, wherein said valve assembly further comprises a mechanism responsive to manual palpation, wherein said mechanism is operable to switch said valve assembly between the first configuration and the second configuration in response to manual palpation.

16. The method of claim 9, wherein said manual pump further comprises a silicone bulb.

17. The method of claim 9, wherein said valve assembly further comprises a mechanism responsive to manual palpation, wherein said mechanism is operable to switch said valve assembly between the first configuration, the second configuration, and the third configuration in response to manual palpation.

18. The method of claim 9, wherein said valve assembly further comprises a mechanism responsive to ultrasound, wherein said valve assembly is operable to be placed in the first configuration in response to a first ultrasound emission, and wherein said valve assembly is operable to be placed in the second configuration in response to a second ultrasound emission.

19. The method of claim 18, wherein said first ultrasound emission is at a first ultrasound frequency, wherein said second ultrasound emission is at a second ultrasound frequency.

20. The method of claim 18, wherein said first ultrasound emission is in a first pattern, wherein said second ultrasound emission is in a second pattern.

* * * * *